(12) United States Patent
Ohishi (10) Patent No.: US 6,990,229 B2
(45) Date of Patent: Jan. 24, 2006

(54) IMAGE PROCESSING DEVICE AND IMAGE PROCESSING METHOD

(75) Inventor: Satoru Ohishi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 94 days.

(21) Appl. No.: 10/421,926

(22) Filed: Apr. 24, 2003

(65) Prior Publication Data

US 2003/0185426 A1   Oct. 2, 2003

Related U.S. Application Data

(63) Continuation of application No. PCT/JP01/09341, filed on Oct. 24, 2001.

(30) Foreign Application Priority Data

Oct. 24, 2000 (JP) .............................. 2000-324411

(51) Int. Cl.
*G06K 9/36* (2006.01)

(52) U.S. Cl. ..................... 382/154; 382/294
(58) Field of Classification Search ................ 382/128, 382/131, 154, 254, 294; 345/419, 426, 629, 345/634, 650, 653, 656, 661, 664, 667
See application file for complete search history.

(56) References Cited

U.S. PATENT DOCUMENTS 5,633,951 A * 5/1997 Moshfeghi .................. 382/154
5,911,691 A * 6/1999 Mochizuki et al. .......... 600/443
5,954,650 A * 9/1999 Saito et al. .................. 600/425
6,252,599 B1 * 6/2001 Natsuko et al. ............. 345/419
6,266,453 B1 * 7/2001 Hibbard et al. ............. 382/294
2002/0172408 A1 * 11/2002 Saito et al. .................. 382/132

FOREIGN PATENT DOCUMENTS

JP   8-212325 A * 8/1996
JP   08-294485 A   11/1996

* cited by examiner

*Primary Examiner*—Andrew W. Johns
(74) *Attorney, Agent, or Firm*—Oblon, Spivak, McClelland, Maier & Neustadt, P.C.

(57) ABSTRACT

A CT device, an MRI device, an ultrasonic device, or an X-ray device for picturing a 3-D image are connected to a network. A 3-D image is stored in an image database via the network. A first image processing device or a second image processing device obtains a 3-D image from the respective devices via the network. The image processing device can display a plurality of 3-D images concurrently with conditions made uniform with regard to direction of observation, enlargement ratio, scale, etc. Also, the device can display a combined image obtained by combining a plurality of 3-D images. The combined image can be displayed so that overlapping areas and non-overlapping areas are in different colors. In addition, the device can display medical information of use for a diagnosis or an examination together with the plurality of 3-D images displayed with conditions made uniform.

24 Claims, 5 Drawing Sheets

IMAGE PROCESSING DEVICE AND IMAGE PROCESSING METHOD

CROSS-REFERENCE TO RELATED APPLICATIONS

This is a Continuation Application of PCT Application No. PCT/JP01/09341, filed Oct. 24, 2001, which was not published under PCT Article 21(2) in English.

This application is based upon and claims the benefit of priority from the prior Japanese Patent Application No. 2000-324411, filed Oct. 24, 2000, the entire contents of which are incorporated herein by reference.

BACKGROUND OF THE INVENTION

1. Field of the Invention

The present invention relates to an image processing device and an image processing method for displaying an image by performing image processing on a medical image obtained from medical image diagnosis devices including an ultrasonic diagnosis device, an X-ray CT device, a magnetic resonance imaging (MRI) device, or a radiopharmaceutical diagnosis device.

2. Description of the Related Art

Conventionally, when a medical image of a patient pictured by a medical image diagnosis device or the like is observed, an image processing device capable of performing image processing and displaying an image in various configurations is used. In particular, an image processing device developed recently performs not only 2-D image processing, but also 3-D image processing, and is thereby able to display an image by creating a pseudo 3-D space in which the depth of an object from a given point of view and shadows generated by a particular light source are calculated as if it were a world seen through the human eye.

In a diagnosis using such an image processing device, there is a case where, for example, two different images are displayed concurrently for comparison. In this case, the images can be compared with each other with relative ease by making angles of observation, enlargement ratios, etc. of the two images equal.

Figure 6:
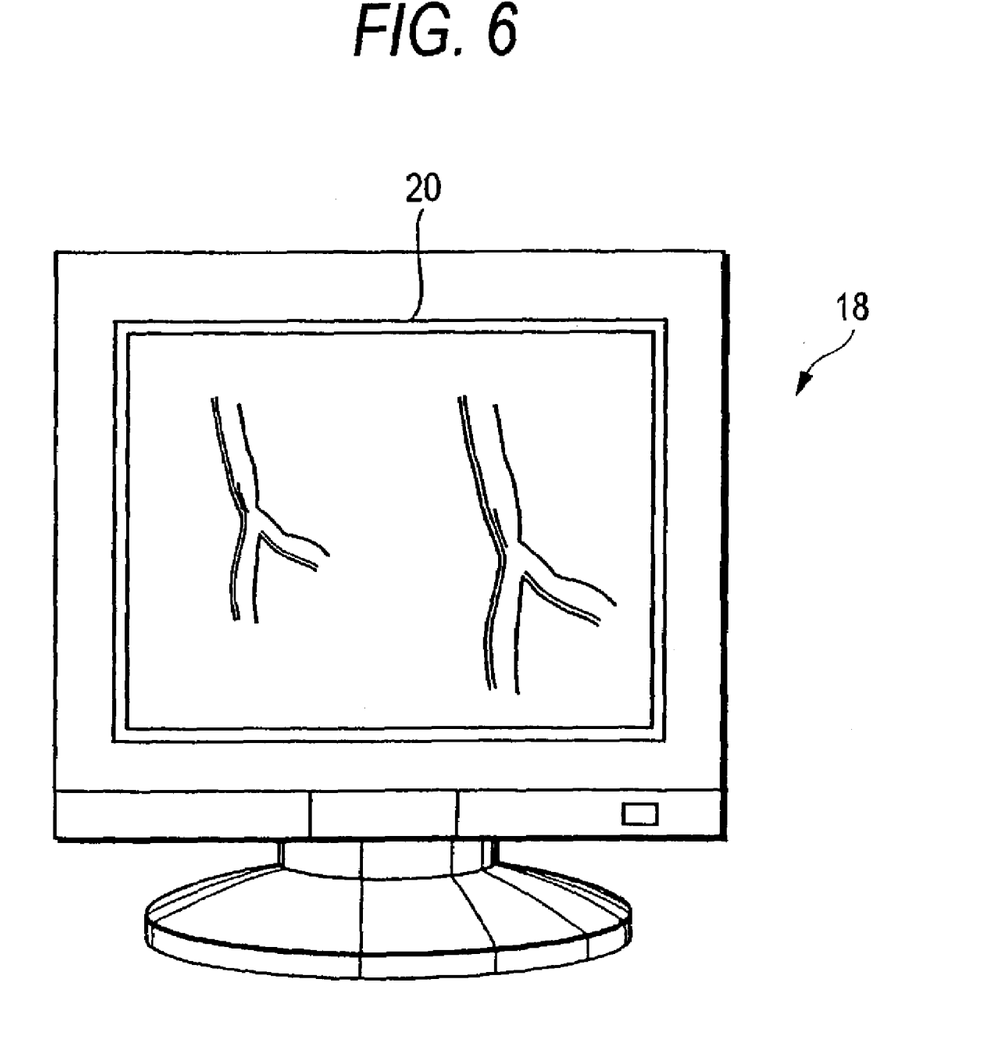
FIG. 6 is a view showing one example of a screen display by a conventional image processing device.

FIG. 6 is a view used to explain a manipulation of a conventional image processing device when two different 3-D images are displayed concurrently for comparison. As shown in FIG. 6, when a plurality of (two, in this case) 3-D images displayed on an image monitor 18 are observed, the angle of observation, the enlargement ratio, the image processing for display, etc. of each image is often set to be the same in order to make comparison easier. Most of the manipulations to make these conditions the same are performed by the user through manual manipulations in the conventional image processing device.

However, not only time and labor, but also proficiency is needed for the manual setting manipulations, and therefore, the image processing device is not easy to use for a typical user. This becomes one of obstacles to propagation of the use of 3-D images for comparisons.

On the other hand, it is widely admitted in the comparative reading of 2-D images of tomographic imaging, such as an X-ray radiograph, CT, and MRI, that comparison of images is a useful examination/diagnosis method in clinical medicine. Judging from this fact, it would appear that comparison of 3-D images would be useful. The advent of an image processing device capable of processing 3-D images for easy comparison with simple manipulations has been long hoped for.

It is therefore an object of the invention to provide a user-friendly image processing device and image processing method capable of displaying images with an agreed-upon angle of observation, etc. automatically or through simple manipulations when displaying a plurality of 3-D images concurrently for comparison while displaying necessary diagnosis information at the same time.

BRIEF SUMMARY OF THE INVENTION

In order to achieve the above and other objects, the invention provides means as follows.

A first aspect of the invention is an image processing device comprising an image processing unit for performing image processing so that angles of observation of a plurality of 3-D images are made equal; and a display device for concurrently displaying the plurality of 3-D images whose angles of observation have been made equal.

A second aspect of the invention is an image processing device comprising an image processing unit for performing image processing so that enlargement ratios of a plurality of 3-D images are made equal; and a display device for concurrently displaying the plurality of 3-D images whose enlargement ratios have been made equal.

A third aspect of the invention is an image processing device comprising an image processing unit for performing image processing for a plurality of 3-D images under same conditions; and a display device for displaying the plurality of 3-D images concurrently.

A fourth aspect of the invention is an image processing device comprising an image processing unit for performing image processing so that a plurality of 3-D images are made equal with respect to at least one of the following: the angle of observation, enlargement ratio, or image processing; an image combining unit for generating a combined image by combining the plurality of 3-D images to which the image processing has been applied; and a display device for displaying the combined image.

A fifth aspect of the invention is an image processing device comprising an image reconstruction unit for generating a plurality of volume data sets by applying image reconstruction processing through the use of a space filter which filters the same conditions to each of the groups of projected images respectively corresponding to each of a plurality of 3-D images; an image processing unit for generating a plurality of 3-D images from each of the volume data sets; and a display device for displaying the plurality of 3-D images concurrently.

A sixth aspect of the invention is an image processing device comprising an image processing unit for processing images to be equal with respect to at least one of the following: angles of observation, enlargement ratios, and image processing of a plurality of 3-D images; a database for storing diagnosis information related to a diagnosis in a past; a diagnosis information management unit for reading out diagnosis information related to at least one of the plurality of 3-D images from the database; and a display device for displaying the plurality of 3-D images to which the image processing has been applied, and at the same time, display the read-out diagnosis information.

A seventh aspect of the invention is an image processing device comprising a display device for displaying a 3-D image or diagnosis information; a database for storing diagnosis information or a 3-D image related to a diagnosis in a past; and a control device for judging the presence of a variance between the 3-D image or diagnosis information being displayed and the diagnosis information or 3-D image of a past diagnosis stored in the database, wherein, in the case where the control device judges that there is a variance, the display device displays an indication that there is a variance or reads out and displays the information or image having the variance from the database.

An eighth aspect of the invention is an image processing method comprising displaying a plurality of 3-D images; performing image processing switching direction of observation of the plurality of 3-D images to that of one preferred image among the plurality of 3-D images, so that the angle of observation of the preferred image and the angles of observation of the rest of the images are made uniform; and displaying the plurality of 3-D images concurrently after the angles of observation are changed.

A ninth aspect of the invention is an image processing method comprising displaying a plurality of 3-D images; performing image processing based on a instruction to change enlargement ratios to that of one preferred image among the plurality of 3-D images, so that the enlargement ratio of the desired one image and enlargement ratios of the rest of the plurality of 3-D images are made uniform; and displaying the plurality of 3-D images concurrently after the enlargement ratios are changed.

A tenth aspect of the invention is an image processing method comprising displaying a plurality of 3-D images; performing image processing based on a instruction to change method of image processing to that of one preferred image among the plurality of 3-D images, so that the image processing of the one preferred image and the image processing of the rest the plurality of 3-D images are made uniform; and displaying the plurality of 3-D images concurrently after the image processing is performed.

DETAILED DESCRIPTION OF THE INVENTION

<First Embodiment>

Figure 1:
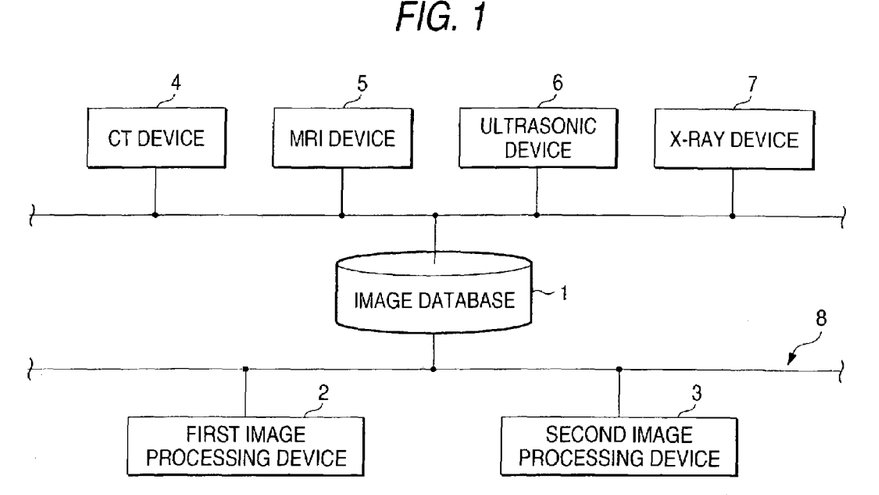
FIG. 1 is a schematic view used to explain an arrangement of an image processing device according to one embodiment of the invention.

FIG. 1 is a schematic view showing a diagnosis system including an image processing device according to a first embodiment of the invention. The diagnosis system includes a first image processing device 2, a second image processing device 3, image diagnosis devices, such as a CT device 4, an MRI device 5, an ultrasonic device 6, an X-ray device 7, or a radiopharmaceutical device, and an image database 1. The respective devices are interconnected via a network 8 to enable data transmission. A 3-D image is reconstructed in each diagnosis device by imaging the internal structure of a patient three-dimensionally, and the image thus generated is stored into the image database 1. It should be noted that not only 3-D images, but also patient and picture condition information, information specifying the orientation of the image, etc. accompanying the image are held in the image database 1.

In this embodiment, a diagnosis system including two image processing devices as shown in FIG. 1 is used as an example. It should be appreciated, however, that the number of image processing devices provided to the system is not limited.

Figure 2:
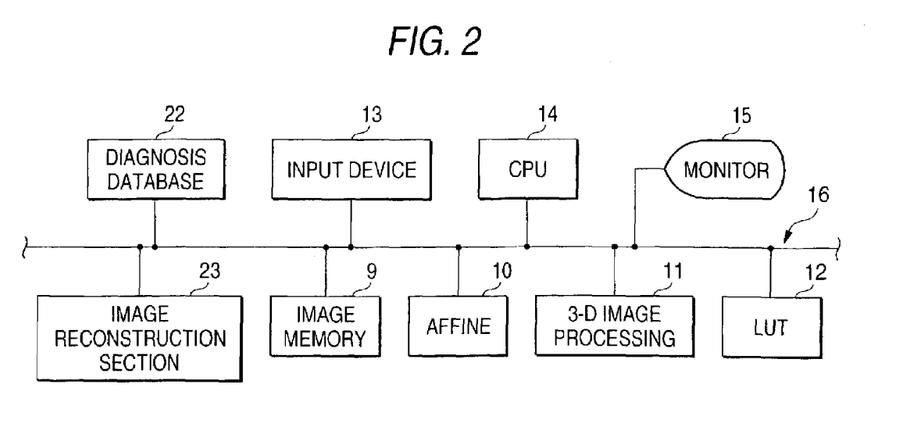
FIG. 2 is a schematic view used to explain an arrangement of an image processing device according to one embodiment of the invention.

FIG. 2 is a schematic view used to explain the internal structure of the first image processing device 2 or the second image processing device 3 shown in FIG. 1. As shown in FIG. 2, the first or second image processing device has a CPU 14, an input device 13, an image memory 9, a 3-D affine processing portion 10, a 3-D image processing portion 11, an LUT (Look Up Table) 12, a display portion (monitor) 15, and a signal bus 16. The functions of the respective components are, for example, as follows.

The CPU 14 controls processing of the overall image processing device.

The input device 13 is a device used to input command information from an operator into the image processing device. The input device 13 is provided with, for example, buttons, a keyboard, a trackball, a joy stick, etc. for setting various display conditions. In image condition uniformity processing described below, a manipulation changing the angle of display, etc. is specified through the input device 13 to at least one of a plurality of images displayed concurrently.

The image memory 9 stores 3-D image data, projected image data before reconstruction, etc.

The 3-D affine processing portion 10 is a transformation portion that applies parallel movement, enlargement, reduction, rotation, etc. (that is, affine transformation) to a display image.

The 3-D image processing portion 11 constructs a 3-D display image by performing 3-D image processing, such as volume rendering processing, and surface rendering processing.

The LUT (Look Up Table) 12 converts the grayscale of a 3-D display image which has been input, based on a conversion correspondence table between an input value and an output value.

The display portion 15 is a monitor that displays a 3-D display image. The display portion 15 has a plurality of display areas and is thereby able to display a plurality of 3-D display images at a time. It may adopt a multi-window display structure or may be composed of a plurality of monitors.

The signal bus 16 sends incoming and outgoing signals or data among the respective components.

A diagnosis database 22 stores diagnosis images (2-D or 3-D images), patient data, examination data, etc. obtained from the image database 1, and from the respective diagnosis devices or the like via the network 8 after marking correlated data. Information stored in the diagnosis database 22 is searchable by items including for example, "regions", "names of diseases", "comment (background of diagnosis)", etc. Also, the diagnosis database 22 is furnished with a dictionary function, automatically managing data by "regions" and "names of diseases".

An image reconstruction portion 23 performs image reconstruction processing based on image data of projection images stored in the memory 9.

Alternatively, the 3-D affine processing 10 and the 3-D image processing 11 may be performed by the CPU 14.

The condition uniformity display processing performed by the first image processing device 2 or the second image processing device 3 will now be explained.

Figure 3:
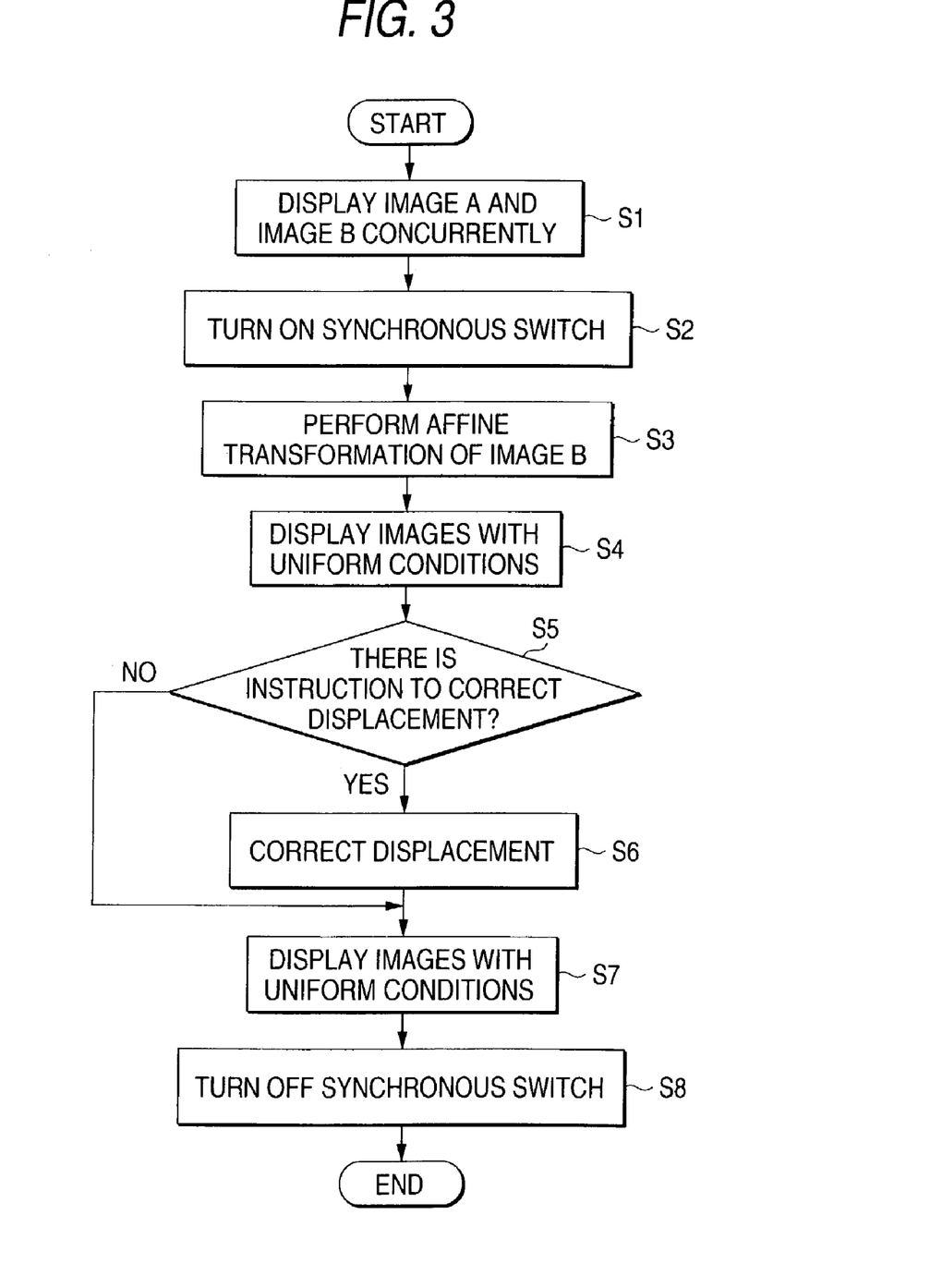
FIG. 3 is a flowchart detailing an example procedure of condition uniformity processing for bringing the conditions of an image A and an image B to be displayed concurrently into uniformity.

FIG. 3 is a flowchart detailing the procedure of the condition uniformity processing to bring the conditions of an image A and an image B to be displayed concurrently into agreement. The following description will describe an example case where the image A and the image B have the same angle of display.

Referring to FIG. 3, the 3-D images A and B registered in the image database 1 are displayed concurrently on the image processing device (Step S1). The 3-D images A and B may be images pictured in the same modality or images pictured in different modalities. It is normal that the respective display images at this stage are generally displayed at different angles unless they have been made to agree intentionally.

Subsequently, a condition uniformity switch is turned ON by the operator (Step S2). In response to this ON-manipulation, in the case where the as-is image A is a controllable image, for example, the image B is subjected to rotational transformation (affine transformation), so that its angle of display agrees with an angle of display of the image A (Step S3). This rotation is performed not to merely make an agreement in quantity of change from the initial angle of display, but to make it possible to observe anatomy of the image B at the same angle as that of the image A, based on various information and on the orientation of the image (hereinafter, information needed to bring the anatomic angles of observation of the image B and the image A into agreement is referred to as the image orientation information).

The image orientation information of the CT device 4 includes the patient insertion direction, an image observation direction, a patient body posture, etc. For example, the patient insertion direction is the image orientation information indicating whether a patient goes into the CT device 4 from the head or from the foot. The patient insertion direction determines the alignment order of 3-D images to be reconstructed, and is expressed as Top First (TF: an image is constructed sequentially in a direction from the top of head)/Foot First (FF: an image is constructed sequentially in a direction from the toe). The image observation direction indicates the direction in which an image is observed, and is expressed as View from Top (VFT: an image viewed in a direction from the top of head)/View from Foot (VFF: an image viewed in a direction from the tiptoe). Further, the patient body posture is the image orientation information indicating the vertical/horizontal orientation of a patient at the time of picturing.

For example, in Step S1, suppose a case where i) both the image A and the image B are at the initial angles of display, ii) the image orientation information of the image A indicates VFT, TF, and upward; and iii) the image orientation information of the image B indicates VFF, FF, and upward. In this case, by performing the affine transformation such that inverts the image B vertically in Step S3, it is possible to bring the angles of observation of the image A and the image B into agreement.

It should be noted that the principle is the same even in the case of an MRI device. However, because the MRI device can set a tomographic layer freely with respect to a patient, it is preferable to use more detailed image orientation information.

The image A and the image B which are made uniform with respect to angle of observation in Step S3 are displayed on the display portion 15 with uniform conditions (Step S4).

Then, it is checked whether there is an instruction to correct a displacement between the 3-D image A and the 3-D image B (Step S5). The displacement correction referred to herein means a function as follows: in making the image condition uniformity through a rotation, a slight change in orientation of a patient before the picturing may possibly cause a difference even in the case where images are displayed at the same angles with respect to the anatomy of the patient based on the image orientation information as described above. According to the image processing device of this embodiment, it is possible to correct a displacement between the images through two kinds of function described below when necessity arises.

One is a function of correcting a displacement between the images by identifying at least two, for example, three anatomically corresponding points on both the images A and B and bringing these points into agreement. For example, let ($^a$A, $^b$A, $^c$A) be the identified points on the image A and ($^a$B, $^b$B, $^c$B) be the identified points on the image B. Further, assume that $^a$A and $^a$B, $^b$A and $^b$B, and $^c$A and $^c$B are the pairs of points that anatomically correspond to each other. Then, it is possible to correct a displacement between the images by calculating in such a manner that straight lines $^a$A$^b$A and $^a$B$^b$B are aligned in the same direction and that straight lines $^a$A$^c$A and $^a$B$^c$B are aligned in the same direction.

The other is a function of correcting a displacement between images through a manual manipulation by the operator. That is, at the time of a manipulation with a button assigned with a specific function kept pressed, for example, at the time of a rotation manipulation with a SHIFT key on the keyboard kept pressed, the rotation processing is performed on only one of the images. A concrete processing operation is the same as the content in Step S3.

In the case an instruction for displacement correction is detected in Step S5, the displacement is corrected through one of the two kinds of correction described above or both (Step S6), and the image A and the image B are displayed again with the conditions agreed (Step S7). In the case where the displacement correction is performed through a manual manipulation, it is preferable that the images are displayed with the conditions in agreement automatically at the instant the SHIFT key is released.

In the case where the displacement correction is performed in Step S6, the quantity of change from the first condition uniformity state is stored as the amount of error; thereafter, error is corrected and the images are displayed with the conditions in agreement the.

On the other hand, in the case where no instruction for displacement correction is detected in Step S5, the image A and the image B are displayed as is with the conditions agreed (Step S7).

Thereafter, processing added to one image, for example, rotation, movement, enlargement/reduction, etc. is applied to the other image in the same manner while the condition uniformity switch stays ON. It should be noted, however, that movement and enlargement/reduction is only a relative change.

Figure 4:
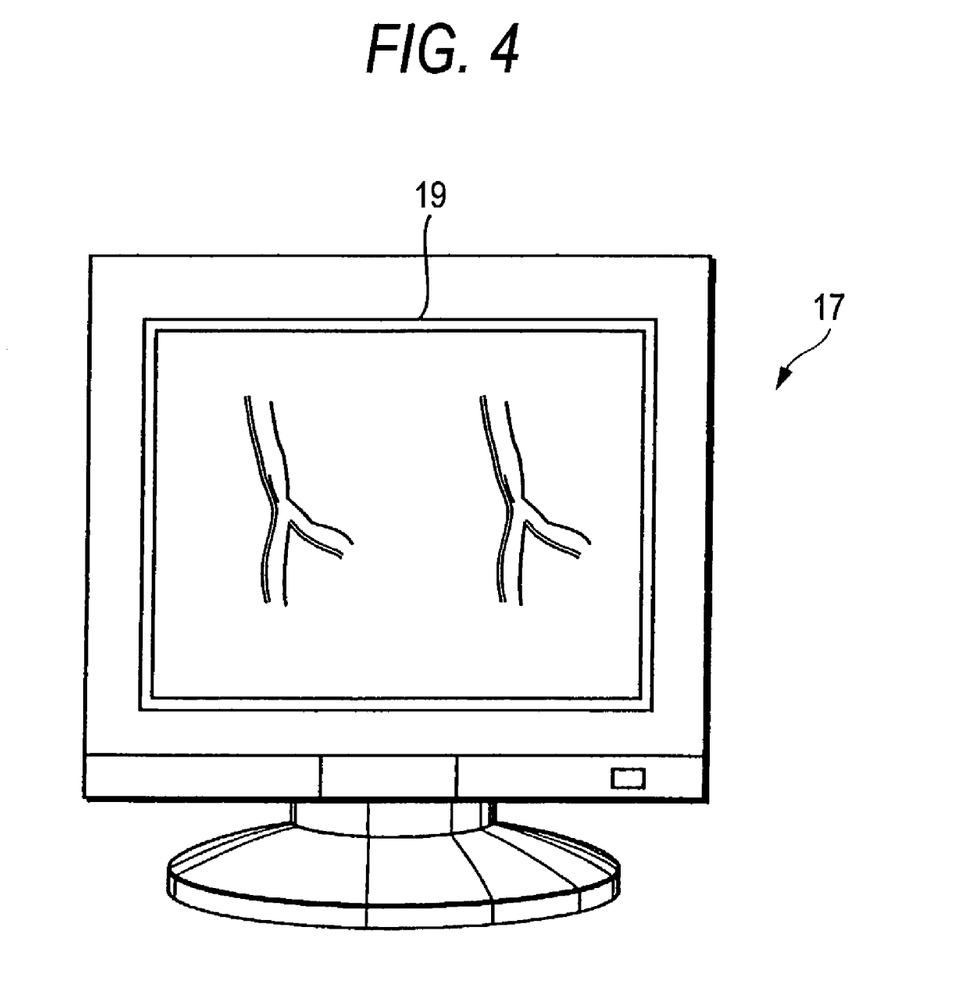
FIG. 4 is a view showing one example of a screen display by an image processing device according to one embodiment of the invention.

FIG. 4 is a view showing one example of 3-D images subjected to image processing by the image processing device of the first embodiment and displayed on the display device 15. As shown in FIG. 4, 3-D images A and B of a region observed are displayed with the conditions in agreement on a display screen 19 of a display monitor 17. When the scale, angle of observation, or enlargement ratio of one of the two images is manipulated, the other 3-D image being displayed is also changed so that the conditions are the same. It is thus possible to compare a plurality of 3-D images with one another under the same conditions all the time.

The condition uniformity display processing is terminated by turning OFF the condition uniformity switch at an arbitrary time, whereupon the condition uniformity state is released (Step S8).

The image processing device of this embodiment, and an image processing device according to each of embodiments described below are also able to operate as follows.

This embodiment describes a case where two 3-D display images are displayed; however, the number of images is not limited, and, for example, three or more images can be displayed. Also, this embodiment described each of the image processing device, the examination device, and the image database 1 as a separate device; however, the arrangement of the invention is not limited to the foregoing arrangement, and the invention is feasible even when two or all of these devices are formed in a single device.

Also, in the embodiment above, image condition uniformity was achieved chiefly with the image orientation information. However, in the case where adequate image orientation information cannot be adopted, as where the 3-D image A and image B are pictured in different modalities, the images may be arranged in such a manner that at least three corresponding points are selected on each image and conditions based on these corresponding points are made uniform.

<Second Embodiment>

A second embodiment of the invention will now be explained with reference to FIG. 3. This embodiment describes the condition uniformity processing in enlargement ratio more in detail. An explanation is omitted for the same arrangements as those in the first embodiment.

Referring to FIG. 3, 3-D images A and B registered in the image database 1 are first displayed three-dimensionally on the image processing device (Step S1). The images A and B may be images pictured in the same modality or may be images pictured in different modalities. In general, the respective display images are different in angle of display and enlargement ratio unless they have expressly been made uniform.

Subsequently, the condition uniformity switch is turned ON by the operator (Step S2).

In response to the ON-input of the condition uniformity switch, the affine transformation is performed to bring the 3-D images A and B into agreement in angle of observation and enlargement ratio (Step S3), and the images are displayed with the conditions agreed automatically (Step S4). Hence, the operator is able to observe images with uniform conditions easily without any tedious procedure.

The transformation processing performed in Step S3 to bring the enlargement ratio into agreement will now be explained. Because the transformation to bring the angle of observation into agreement is the same as that in the first embodiment, an explanation is omitted herein.

To bring the enlargement ratio into agreement means displaying the actual lengths which are equal with images of the same length on the display device. For example, assuming that the initial image A is a controllable image, then the image B is rotated, so that the angle of display and the enlargement ratio agree with the angle of display of the image A. This is done not to merely make an agreement in change from the initial angle of display and the initial enlargement ratio, but to transform the portions of the same actual length into images of the same length on the display device, to enable observation at the same angles in terms of the anatomy of the patient by taking the image orientation and the pixel pitch into account.

For example, in the case of a CT device, the pixel pitch in the tomographic layer is determined by the various picturing conditions, that is, the pictured area and the matrix size, and the pixel pitch in the body axial direction is determined by range of movement of the patient couch (in the case of the helical scan method, movement speed of the patient couch), width of the collimator, etc. It is assumed here that 0.5 mm is the pixel pitch in both the tomographic layer and the body axial direction of the image A, and 0.7 mm is the pixel pitch in both the tomographic layer and the body axial direction of the image B. In this case, even when exactly the same region is pictured, the image A is displayed 1.4 times larger than the image B in the initial state.

According to the uniformity function for enlargement ratio of this embodiment, correction is performed by also taking this pixel pitch into account. That is, in the case of this example, assume that the image A is controllable and is displayed 1.2 times larger than the current initial display state, then the image B is displayed after being enlarged by 1.68 (=1.2×1.4) times.

It should be noted, however, that, movement provides only a relative change. That is, in the case where one image is moved by 5 mm in the z-axis direction, the other image is moved by 5 mm in the z-axis direction as well.

The image A and the image B whose enlargement ratios are made uniform in Step S3 are displayed on the display portion 15 with uniform conditions (Step S4). As with the first embodiment, processing added to one image, for example, rotation, movement, enlargement/reduction, etc., is applied to the other image in the same manner while the condition uniformity switch stays ON.

Subsequently, it is checked whether there is an instruction to correct a displacement between the 3-D image A and the 3-D image B (Step S5). That is, in regard to rotation and enlargement, a slight change in orientation of a patient before the picturing, distortion of pictured images, etc. may possibly cause a difference in angle of observation and enlargement ratio even in the case where images displayed at the same angles in terms of anatomy and the same enlargement ratio are being displayed. Because the correction methods of the angle of observation were explained in the first embodiment, the following description will describe only the correction of an enlargement ratio performed by the image processing device according to this embodiment.

The image processing device according to this embodiment is furnished with two kinds of function for correcting such a displacement. One is a function of identifying two anatomically matching points on both the images A and B and correcting a displacement between the images based on these points. For example, two points out of the points identified for specifying an error in angle, ($^a$A, $^b$A) on the image A and ($^a$B, $^b$B) on the image B, may be used, or when the absence of an error in angle is judged, only two points, ($^a$A, $^b$A) on the image A and ($^a$B, $^b$B) on the image B, need be identified. Herein, it is possible to correct displacement between the images by calculating an enlargement ratio in such a manner that straight lines $^a$A$^b$A and $^a$B$^b$B are of the same length.

The other is a function by manual manipulation, and at the time of a manipulation with a button assigned with a specific function kept pressed, for example at the time of an enlargement manipulation with a SHIFT key on the keyboard kept pressed, the processing is performed on only one of the images.

In the case where an instruction for displacement correction is detected in Step S5, the displacement is corrected through at least one of the two kinds of correction described above (Step S6), and the image A and the image B are displayed again with uniform conditions (Step S7). In the case where the displacement correction is performed through a manual manipulation, it is preferable that the images are displayed with the conditions made uniform automatically at the instant the SHIFT key is released.

In the case where the displacement correction is performed in Step S6, a quantity of change from the first condition uniformity state is stored as the error amount; thereafter, the error is corrected and then the images are displayed with uniform conditions (Step S7).

On the other hand, in the case where there is no instruction for displacement correction in Step S5, the image A and the image B are displayed as is with uniform conditions (Step S7).

In order to terminate the condition uniformity, the condition uniformity state is released by turning OFF the condition uniformity switch (Step S8).

The above description described the condition uniformity processing operation of the image processing device according to the second embodiment. As with the first embodiment, the image processing device of this embodiment stores the quantity of change from the first condition uniformity state as the error amount when the displacement correction is performed, and is thus able to display images thereafter with uniform conditions after the error is corrected. Also, the number of images is not limited, and three or more images can be processed concurrently.

<Third Embodiment>

An image processing device according to a third embodiment will now be explained. This embodiment describes a case where image processing is performed under the same conditions for the respective images to be displayed with uniform conditions. The arrangement of the image processing device according to the third embodiment is substantially the same as that of the image processing device described in the first embodiment. Also, an explanation is omitted for the portions that overlap those in the first and second embodiments described above.

The condition uniformity processing of the respective image processing devices according to the third embodiment will now be explained with reference to FIG. 5.

Figure 5:
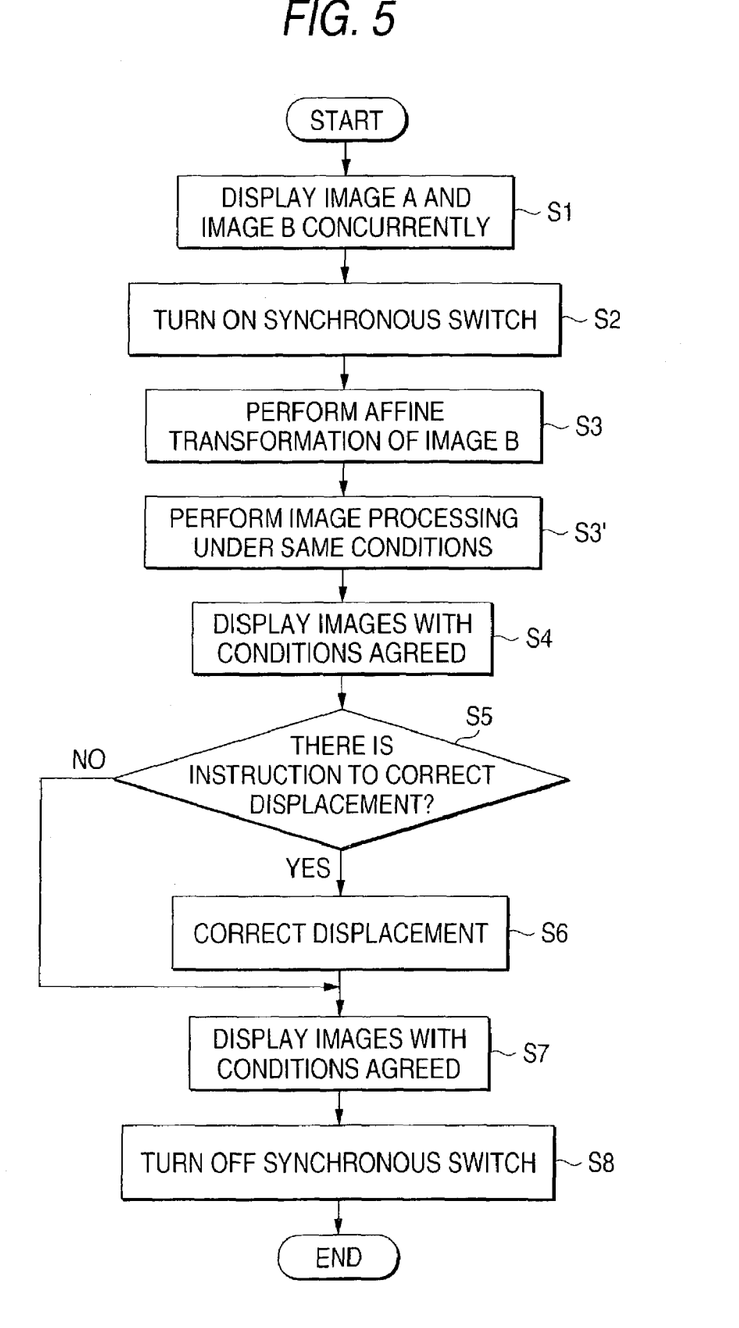
FIG. 5 is a flowchart detailing another example procedure of condition uniformity processing for bringing the conditions of an image A and an image B to be displayed concurrently into uniformity.

Referring to FIG. 5, as with the first embodiment, an image A and an image B are first displayed concurrently (Step S1), and the condition uniformity switch is turned ON (Step S2).

In response to the ON-manipulation in Step S2, assuming that the as-is image A is a controllable image, the image B is subjected to rotation transformation or the like, so that the angle of display and the image processing for display agree with the angle of display and the image processing for display of the image A. This is done not to merely make an agreement in quantity of change from the initial angle of display and the initial image processing for display, but to make a change such that enables observation of the same anatomical features at the same angles by taking the orientation of the image into account.

Subsequently, image processing is applied to the image A or the image B or both, so that the image processing for display of the image A and the image B will be exactly the same processing (Step S3'). The following description will describe more in detail typical two kinds of image processing by way of example.

According to the surface rendering method, a threshold is set, and an area that falls within the range of the threshold is deemed as a subject area. Then, pseudo computation is performed as if light was irradiated to the subject from an arbitrary direction, and a display image is calculated by computing reflected light. In Step S3' of this embodiment, processing is performed in such a manner that the threshold, the position and the intensity of the light source, a color of the subject, etc. in this instance are the same.

In the case of the volume rendering method, a function (optical converting function) that converts the number of pixels into an optical parameter such as reflectance index or refraction index, is defined. Then, display image data is computed by positing irradiating light to the object from a chosen direction and calculating reflected light. According to the volume rendering method, it is possible to make the internal structure appear blurred as though seen through a fog, for example, depending on the definition of the optical converting function. Hence, different from the surface rendering method, the surface of the object can be defined clearly, and information hidden behind the surface can be imaged.

In Step S3' of this embodiment, the processing is performed in such a manner that the optical converting function, the position and the intensity of the light source, the color of the subject, etc. are uniform.

Thereafter, as with the first embodiment, displacement between the image A and the image B is corrected as needed (Steps S5 and S6), and the images are displayed with uniform conditions (Step S4 and Step S7). The condition uniformity display is released by turning OFF the switch (Step S8), whereupon the condition uniformity display processing is completed.

<Fourth Embodiment>

An image processing device according to a fourth embodiment will now be explained. This embodiment describes a modification when the same image processing is performed. The arrangement of the image processing device according to the fourth embodiment is substantially the same as that of the image processing device described in the first embodiment. Also, an explanation is omitted for portions that overlap those explained in the respective embodiments above.

The following description will describe the condition uniformity processing of the respective image processing devices according to the fourth embodiment with reference to FIG. 5.

Referring to FIG. 5, as with the first embodiment, an image A and an image B are first displayed concurrently (Step S1), and the condition uniformity switch is turned ON (Step S2).

In response to the ON-manipulation in Step S2, assuming that the as-is image A is a controllable image, then the image B is subjected to rotation transformation or the like, so that the angle of display and the image processing for display agree with the angle of display and the image processing for display of the image A. This is done not to merely make an agreement in quantity of change from the initial angle of display and the initial image processing for display, but to make a change such that enables observation of anatomical features at the same angles and in the same size by taking the orientation of the image into account.

Subsequently, image processing is applied to the image A or the image B or both, so that the image processing for display of the image A and the image B will be exactly the same (Step S3'). For example, the image processing of the image A and that of the image B are made the same by correcting an optical converting function of the image B based on the pixel pitch as follows.

For example, let m be the pixel pitch of the image B and n be the pixel pitch of the image A. Then, the optical converting function of the image B is corrected with a function as follows.

$$a=(1-\exp[-nN])/(1-\exp[-mN])$$

Herein, reflectance index $\gamma$ is modeled by the equation below, and N is a pixel value.

$$\gamma=1-\exp[-xN]$$

Herein, x is the passing distance of the subject.

When the image processing is performed with the above-described optical converting function in Step S3', as with the first embodiment, the displacement between the image A and the image B is then corrected as needed (Steps S5 and S6), and the images are displayed with uniform conditions (Step S4 and Step S7). The condition uniformity display is released by turning OFF the switch (Step S8), whereupon the condition uniformity display processing is completed.

<Fifth Embodiment>

An image processing device according to a fifth embodiment will now be explained. The device according to this embodiment is able to combine 3-D images A and B displayed concurrently and display the combined image. The combination can be performed at any desired time.

For example, the 3-D images A and B are combined by pressing a switch for specifying combination in a state of display with uniform conditions in Step S4 shown in FIG. 3 and FIG. 5. Alternatively, a series of processes may be performed, by which three-dimensional combination is performed after a correction matches specified points on the respective images through a single switch manipulation. Further, in the display with uniform conditions, original displacement in angle, displacement in position, and displacement in enlargement ratio between the images is saved so that when the combination switch is pressed, combination is performed after correction is made bringing the angles of display, the positions, and the enlargement ratios into agreement.

<Sixth Embodiment>

An image processing device according to a sixth embodiment will now be explained. This embodiment describes a modification when image combination processing is performed.

In general, according to the volume rendering method, the pixel value is converted into an optical parameter such as reflectance and refractive index, and a display image is calculated on the assumption that light is irradiated to an object constructed with these optical parameters. The combination described in the fifth embodiment is performed by putting every other pixel of one image between every other pixel of another image to form a single image.

However, the combination is not limited to the foregoing, and for example, the optical parameter of a combined image may be calculated as set forth below, using converted optical parameters $\mu A$ and $\mu B$ of the image A and the image B, respectively.

$$\mu=f(\mu A, \mu B)$$

Herein, f is an arbitrary function, and, for example, is used in two ways as follows.

$$\mu=\mu A+\mu B$$

or $$\mu=\mu A-\mu B$$

By using the former, it is possible to obtain an image with a satisfactory resolution. On the other hand, by using the latter it is possible to observe a difference between the image A and the image B clearly.

Alternatively, as another modification, the images may be processed as separate images and then combined on the display lines instead of the method of combining the optical parameters. In this case, it is possible to distinguish one image from the other clearly even in a combined image by setting different colors, intensities and positions of the light source, etc. for the respective images.

Also, in the case using different colors for the respective images, for example a range of the pixel value is specified, then an area that falls within the range is determined, and different colors may be given to an area-overlapping portion and to an area-non-overlapping portion. This makes it possible to distinguish one image from the other clearly in the region in question.

According to the image processing device of this embodiment, it is possible to fuse and display three or more images. For example, in the case where three images A, B, and C are combined, let $\mu A$, $\mu B$, and $\mu C$ be the optical parameters of the respective images, then it is possible to adopt an optical parameter $\mu$ found as follows:

$$\mu=2\mu C-\mu A+\mu B$$

<Seventh Embodiment>

A seventh embodiment describes an image processing device capable of providing a 3-D image useful in diagnosing by performing image reconstruction for a plurality of images displayed concurrently under the same conditions.

For example, an X-ray CT device generates a 3-D image through collection processing of a plurality of projection images of a plurality of cross sections, image reconstruction processing based on this plurality of projection images, image processing of the reconstructed images, etc. In particular, edge emphasis processing using a space filter is also performed in the image reconstruction processing. The space filter is achieved by convolution computation or the like. Hence, in the case where 3-D images A and B reconstructed at different times are displayed concurrently, a difference between the two images due to the difference of parameters of the space filters may appear.

The image processing device according to this embodiment is able to provide 3-D images that are easily compared because reconstruction processing is done under the same conditions. That is, for example, in Step S3' of FIG. 5, the image reconstruction portion 23 performs image reconstruction of projection images corresponding to the image B under the same conditions as those of the image A. By performing the affine transformation to display images again with uniform conditions after the image reconstruction, it is possible to display a plurality of 3-D images to which edge emphasis processing has been applied under uniform conditions.

<Eighth Embodiment>

An eighth embodiment discloses an image processing device capable of providing medical information useful in diagnosing through the use of a 3-D image.

The first or second image processing devices 2, 3 hold diagnosis images (2-D or 3-D images), patient data, examination data, etc. in the diagnosis database 22, giving them markers correlating one with another. As has been described, the information stored in the diagnosis database 22 is searchable by category, such as regions, names of diseases, comment (steps leading to diagnosis). Also, the diagnosis database 22 is furnished with a dictionary function of automatically managing data according to regions or names of diseases.

According to the image processing device of this embodiment, for example, a diagnosis as described below can be performed with a 3-D image through the use of the diagnosis database 22 constructed in this manner. That is, in the case where new diagnosis information, such as a 3-D image and an examination result, is obtained at the time of diagnosis, a search can be conducted through the past data in the diagnosis database 22 based on the name of patient, the region, the name of the disease, etc. related to this diagnosis information. Also, the image or diagnosis information currently displayed and the information in the diagnosis database 22 are compared by the CPU 14 from time to time. In the case where a variance is found by this comparison, the information in the database 22 is read out, and displayed on the display portion 15. More specifically, it is used in the situation as follows.

For example, when there is diagnosis information for the region subjected to diagnosis (or a related region) in the diagnosis database 22, the content (for example, "the date of diagnosis", "the diagnostician", "case", "region", etc.) is presented in the form of a pop-up window on the display portion 15. Further, when one wishes to observe the detail, the content of examination, the result thereof (for example, background information for the diagnosis) in the form of an image or the like are read out from the diagnosis database 22 by pressing a detail button within the window. Hence, the operator can readily read out past 3-D images and related information useful for diagnosis for reference.

Also, for example, when the operator inputs a comment different from the comment accompanying the image of the same patient in the past stored in the database 22 for a 3-D image currently displayed, an indication is automatically displayed on the display portion 15 in the form of a pop-up window or the like, so that the operator may notice the difference. When the operator wishes to know the content of the difference more in detail, the information in the database 22 can be displayed through a predetermined manipulation.

Further, assume that CAD (Computer Aided Diagnostics) was applied to an image in the past, and CAD processing is applied also with the same parameters to an image currently displayed. In this case, there may be a variance in the automatic diagnosis result at the image level between the past and the present depending on a treatment situation. In this instance, the CPU 14 identifies the variance, and indicates the variance to the operator on the display device 15. The operator is assisted in making comparisons by this function, and is thus able to perform a high quality diagnosis more efficiently.

With the image processing devices according to the respective embodiments described above, images can be displayed with the same angle of observation, enlargement ratio, and image processing for display through calculations based on the picturing conditions and the display parameters unique to the particular picturing device by turning ON the condition uniformity switch. Hence, 3-D images can be compared readily, thereby making it possible to confirm the change of an affected area over time and the curative effect.

Also, by turning ON the condition uniformity switch, it is possible to make the angle of observation uniform based on the picturing angle information unique to each picturing device.

Also, the angle of observation and enlargement ratio can be made uniform based on the picturing information unique to each picturing device, and therefore, it is possible to display images with uniform angle of observation, enlargement ratio, and image processing for display based on the picturing conditions unique to each picturing device and the display parameters.

Further, the diagnosis information in the past related to the diagnosis image can be readily provided. As a consequence, it is possible to improve the workability and the quality of a diagnosis.

It should be appreciated that the embodiments described above are provided for the purpose of making it easier to understand the invention, and have no intention to limit the invention. Hence, it is to be understood that the respective elements disclosed in the embodiments above include all design changes and equivalent items that fall within the technical scope of the invention.

As has been described, according to the invention, it is possible to provide a user-friendly image processing device and image processing method capable of displaying images with conditions such as angle of observation made uniform automatically or through a simple manipulation in the case of displaying a plurality of 3-D images concurrently for comparison while displaying necessary diagnosis information at the same time.

What is claimed is:

1. An image processing device, comprising:
    an image processing unit for performing image processing so that angles of observation of a plurality of 3-D images are made equal; and
    a display device for concurrently displaying said plurality of 3-D images whose angles of observation have been made equal.

2. The image processing device according to claim 1, wherein said image processing unit performs said image processing based on position information defined in a picturing device through which each of said 3-D images is obtained.

3. The image processing device according to claim 1, further comprising:
    an interface for inputting an instruction to switch the direction of observation to that of one preferred image among said plurality of displayed 3-D images, wherein:
    said image processing unit performs image processing that makes uniform the angle of observation of said preferred image and the angles of observation of the rest of said plurality of 3-D images when said switching instruction is inputted; and
    said display device displays said plurality of 3-D images concurrently after the angles of observation are changed.

4. The image processing device according to claim 1 or 3, wherein said image processing unit performs said image processing by making a correspondence between coordinates of at least two points specified in each of said 3-D images.

5. The image processing device according to claim 3, wherein said image processing unit performs said image processing based on position information of the picturing device through which each of said 3-D images is obtained.

6. The image processing device according to claim 3, wherein said image processing unit performs said image processing based on an instruction inputted manually through said interface.

7. The image processing device according to claim 1, wherein:
said image processing unit performs image processing so that enlargement ratios of a plurality of 3-D images are made equal; and
said display device concurrently displays said plurality of 3-D images whose enlargement ratios have been made equal.

8. The image processing device according to claim 7, wherein said image processing unit performs said image processing based on the conditions of the picturing device through which each of said 3-D images was obtained.

9. The image processing device according to claim 7, further comprising:
an interface for inputting an instruction switching the enlargement ratio to that of one preferred image among said plurality of 3-D images being displayed, wherein:
said image processing unit performs image processing that makes uniform the enlargement ratio of said preferred image and the enlargement ratios of the rest of said plurality of 3-D images when said switching instruction is inputted; and
said display device displays said plurality of 3-D images concurrently after the enlargement ratios are changed.

10. The image processing device according to claim 7 or 9, wherein said image processing unit performs said image processing by making a correspondence of information based on coordinates of at least two points specified in each of said 3-D images.

11. The image processing device according to claim 9, wherein said image processing unit performs said image processing based on the conditions of the picturing device through which each of said 3-D images is obtained.

12. The image processing device according to claim 9, wherein said image processing unit performs said image processing based on an instruction inputted manually through said interface.

13. The image processing device according to claim 1, wherein:
said image processing unit performs image processing for a plurality of 3-D images under the same conditions; and
said display device displays said plurality of 3-D images concurrently.

14. The image processing device according to claim 13, wherein:
said image processing is volume rendering processing; and
said image processing unit performs said image processing so that images are uniform with respect to at least one of the following: image display method, position of the light source, intensity of the light source, optical converting function, and display color.

15. An image processing device, comprising:
an image processing unit for performing image processing so that a plurality of 3-D images are uniform with respect to at least an angle of observation;
an image combining unit for generating a combined image by combining said plurality of 3-D images to which image processing has been applied; and
a display device for displaying said combined image.

16. The image processing device according to claim 15, wherein said image combining unit generates said combined image based on a combined optical parameter set calculated from the optical parameters of each of said plurality of 3-D images.

17. The image processing device according to claim 15, wherein said image combining unit generates a combined image in which the colors given to an area where 3-D images are overlapped and the colors given to an area where 3-D images are not overlapped are different.

18. An image processing device, comprising:
an image processing unit for performing image processing so that a plurality of 3-D images are made uniform with respect to at least one of the following: angle of observation, enlargement ratio, and image processing;
a database for storing information related to a past diagnosis;
a diagnosis information management unit for reading out diagnosis information related to at least one of said plurality of 3-D images from said database; and
a display device for displaying said plurality of 3-D images to which the image processing has been applied, and at a same time displaying said read-out diagnosis information.

19. The image processing device according to claim 18, further comprising:
an interface for inputting an instruction to change at least one of the following: angle of observation, an enlargement ratio, and image processing, to that of one preferred image among said plurality of 3-D images being displayed, wherein:
said image processing unit performs image processing that makes uniform said preferred image and the rest of said plurality of 3-D images with respect to at least one of the following: angle of observation, enlargement ratio, and image processing when said change instruction is inputted; and
said display device displays said plurality of 3-D images concurrently after said changing is performed.

20. An image processing method, comprising:
displaying a plurality of 3-D images;
performing image processing based on a instruction to change the direction of observation to that of one preferred image among said plurality of 3-D images, so that the angle of observation of said preferred image and the angles of observation of the rest of said plurality of 3-D images are made uniform; and
displaying said plurality of 3-D images concurrently after the angles of observation are changed.

21. The image processing method according to claim 20, wherein said image processing is performed based on position information characteristic of the picturing device through which each of said 3-D images is obtained.

22. The image processing method according to claim 20, wherein said image processing is performed based on a correspondence between coordinates of at least two points specified in each of said 3-D images.

23. The image processing method according to claim 20, wherein:
said performing image processing is based on an instruction to change the image processing to that of one preferred image among said plurality of 3-D images, so that image processing on said one desired image and image processing on the rest of said plurality of 3-D images are performed uniformly; and said displaying said plurality of 3-D images is performed concurrently after said image processing is performed.

24. The image processing method according to claim 23, wherein:
said image processing is volume rendering processing; and said change instruction is an instruction to change at least one of the following: image display method, position of a light source, intensity of the light source, optical converting function, and display color.

* * * * *